United States Patent [19]

Legros et al.

[11] Patent Number: 5,362,771
[45] Date of Patent: Nov. 8, 1994

[54] PROCESS FOR INCLUSION IN (METH)ACRYLIC RESINS OF SUBSTANCES OF LIQUID TO SOLID CONSISTENCY

[75] Inventors: Robert Legros, Monceaux; Bernard Wiegert, Brenouille; Jean-Luc Zeh, Spicheren, all of France

[73] Assignee: Elf Atochem, S.A., Paris, France

[21] Appl. No.: 18,228

[22] Filed: Feb. 16, 1993

[30] Foreign Application Priority Data

Feb. 13, 1992 [FR] France ................... 92 01638

[51] Int. Cl.$^5$ ................. C08K 9/10; G21F 9/00; G21F 9/16; C08F 4/06
[52] U.S. Cl. .................. 523/375; 523/113; 526/318.41; 526/332; 588/7
[58] Field of Search ............ 523/375, 112, 113, 115, 523/205; 526/92, 109, 141, 184, 227, 318.41, 327, 328.5, 332; 252/628, 631

[56] References Cited

U.S. PATENT DOCUMENTS

| | | | |
|---|---|---|---|
| 4,077,901 | 3/1978 | Arnold et al. | 523/375 |
| 4,253,985 | 3/1981 | Filter et al. | 523/375 |
| 4,486,179 | 12/1984 | Brauer et al. | 523/115 |
| 4,628,112 | 12/1986 | Winkel et al. | 526/204 |
| 5,063,269 | 11/1991 | Hung | 524/296 |

FOREIGN PATENT DOCUMENTS

| | | |
|---|---|---|
| 0017937 | 10/1980 | European Pat. Off. . |
| 0315462 | 5/1989 | European Pat. Off. . |
| 3505886 | 8/1985 | Germany . |
| 2093854 | 9/1982 | United Kingdom . |

OTHER PUBLICATIONS

World Patents Index Latest, Derwent Publications Ltd., London, AN 84-091813 (abstract of JP-A-59 038 698, Mar. 2, 1984).
World Patents Index Latest, Derwent Publications Ltd., London, AN 86-185538 (abstract of JP-A-61 117 496, Nov. 14, 1984).

*Primary Examiner*—Paul R. Michl
*Assistant Examiner*—Tae H. Yoon
*Attorney, Agent, or Firm*—Millen, White, Zelano & Branigan

[57] ABSTRACT

Inclusion blocks of a substance chosen from ion exchange resins contaminated with radioactive elements, water which can, where appropriate, contain pollutants, solid-phase wastes in the form of blocks or pulverised preparations or liquid-phase wastes are prepared. For this purpose, the substances(s) to be included is/are embedded in a (meth)acrylic resin obtained in situ by direct polymerisation, without prior preparation of a prepolymer syrup, using a monomer system based on at least one (meth)acrylic monomer possessing a high boiling point, such as dicyclopentadienyloxyethyl methacrylate.

Application to the storage of industrial pollutants, in particular substances contaminated with radioactive elements; and application of the water-inclusion blocks as prosthesis materials.

19 Claims, No Drawings

PROCESS FOR INCLUSION IN (METH)ACRYLIC RESINS OF SUBSTANCES OF LIQUID TO SOLID CONSISTENCY

The present invention relates to the inclusion, within (meth)acrylic resins, of various substances having a liquid to solid consistency. This inclusion process makes it possible to obtain new composite materials, such as materials containing water included in the form of globules or nodules, which are applicable, inter alia, in the field of bone and dental prostheses. The inclusion process also makes possible the entrapment of various industrial wastes, such as mercurial wastes and contaminated wastes comprising cation and anion exchanger materials, consisting, for example, of cation exchange resins or of a mixture of cation and anion exchange resins contaminated with radioactive elements.

These resins are, in particular, resins polystyrene crosslinked with divinylbenzene which contain sulphonic groups $SO_3H$ (cation exchange resins), or a mixture of such resins with resins of polystyrene crosslinked with divinylbenzene which contain OH functions bound to a quaternary ammonium group (anion exchange resins).

When cation exchange resins are used to purify contaminated waters, in particular nuclear installation effluents, they undergo degradation and saturation phenomena after a certain period of time and consequently lose their efficacy. These spent ion exchange resins, which have bound a number of radio elements in the course of their use, have then to be entrapped while ensuring good retention of their radioactivity.

It is known to incorporate ion exchange resins contaminated with radioactive elements in thermosetting resins which can be polymerised at room temperature. These resins, which consist, for example, of an unsaturated polyester or an epoxide resin, are polymerised so as to obtain a solid block. However, this process, which is perfectly satisfactory for anion exchange resins, cannot be used according to the same procedure for cation exchange resins which are not completely spent, that is to say which still contain $H^+$ ions which are capable of consuming some of the reactants used for the setting of the resin.

To solve this problem, it has been proposed to subject the incompletely saturated, spent ion exchange resins to a pretreatment by means of an aqueous solution of a basic compound capable of blocking the active sites of the cation exchange resins. However, the implementation of such a pretreatment in the liquid phase has various drawbacks. In effect, it necessitates an additional pretreatment plant upstream of the entrapment plant, and it gives rise, furthermore, to the production of contaminated effluents resulting from the release into the liquid pretreatment phase of a portion of the radio-elements which were bound to the ion exchange resins.

Moreover, it should be stressed that the process of entrapment of contaminated wastes comprising ion exchange resins using polyester or epoxide resins yields an embedded material which possesses mechanical characteristics which are not satisfactory. In effect, it is essential that the finished material should possess good mechanical characteristics that make it possible for it to be capable of aging over time without undergoing mechanical modifications to an excessive extent.

The need hence arises to develop an inclusion process which enables all the drawbacks of the previous processes to be avoided. Generally speaking, it has been seen to be advantageous to be able to have at one's disposal a process for inclusion of wastes of all types, solid and/or liquid, inter alia, of aqueous systems not necessarily containing pollutants. In effect, the good mechanical characteristics of water-inclusion blocks make the latter advantageous as new composite materials.

The subject of the present invention is hence, in the first place, a process for inclusion in a resin of at least one substance of liquid to solid consistency, characterised in that the substance(s) to be included is/are embedded in a (meth)acrylic resin obtained in situ by direct polymerisation, without prior preparation of a prepolymer syrup, using a monomer system based on at least one (meth)acrylic monomer possessing a high boiling point.

According to an especially preferred embodiment, a monomer system is used based on at least one (meth)acrylic monomer having a high boiling point, chosen from dicyclopentadienyloxyethyl methacrylate (DCPOEMA) and its epoxidised homologue (base monomer), where appropriate in the presence of at least one crosslinking monomer chosen, in particular, from di- and tri(meth)acrylates, such as trimethylolpropane trimethacrylate, hexanediol diacrylate, trimethylolpropaneoxyethyl triacrylate, glyceroltrioxypropyl triacrylate, ethylene glycol dimethacrylate and tripropylene glycol diacrylate.

The monomer system can also contain at least one additional comonomer chosen from isobornyl methacrylate or acrylate and acrylic or methacrylic acid.

According to the invention, the (meth)acrylic monomers employed for the process have high boiling points. For the base monomer or monomers, it is between 330° and 380° C. (760 mmHg); for the crosslinking monomer or monomers, the boiling point varies between 250° and 350° C., and for the additional monomer or monomers, around 270° C.

It is also possible to add to the monomer system at least one thickening agent chosen from (meth)acrylic oligomers such as bisphenol diglycidyl dimethacrylate and bisphenol diglycidyl fumarate.

Thus, in order to thicken the medium considerably in order to avoid possible settling of solid wastes in the form of fine particles, it has been, inter alia, possible to mix with DCPOEMA up to 30% by weight of acrylic or methacrylic oligomers such as bisphenol diglycidyl dimethacrylate or up to 20% by weight of bisphenol diglycidyl fumarate.

In a known manner, a monomer system is used containing at least one polymerisation initiator chosen from a peroxide, namely benzoyl or lauryl peroxide, and a percarbonate, for example an alkyl percarbonate, and at least one activator chosen conventionally from tertiary amines, namely trimethylamine, dimethyl-para-toluidine and tetramethylaniline, used individually or mixed, or from organometallic activators, namely those containing cobalt, zirconium or vanadium. The initiator or initiators is/are generally used in a proportion of 0.5 to 5% by weight relative to the weight of all the other constituents of the reaction mixture. The activators, for their part, are used in an amount between 0.01 and 4% by weight relative to the weight of the other constituents of the reaction mixture. Free-radical initiation with the benzoyl peroxide/dimethyl-para-toluidine catalytic system may be performed at low temperature, between 5 and 30° C.

It is also possible to employ, in a known manner, transfer agents such as dodecyl mercaptan, as well as emulsifying agents and surfactants.

The process according to the present invention consists in adding, in a metal reactor, for example, the monomers, the substance or substances to be included, of the liquid, sludge or pulverised type, with stirring, then a polymerisation initiator, an activator and, optionally, a transfer agent. The temperature of the stirred mixture rises at most to 100° C. after a period of time equal to not more than 40 minutes. When polymerisation is complete, the finished product is advantageously cured at a temperature of between 50° and 85° C. for 2 to 15 hours.

In the case where it is desired to include solid substances in the form of blocks, the latter are covered with the polymerisation reaction mixture prepared as above. Depending on the temperature of the medium, setting takes place in a lapse of time of the order of 5–60 minutes.

According to the present invention, it is possible, for example, to prepare an inclusion block of a substance chosen from:
- ion exchange resins contaminated with radioactive elements, as described in greater detail above;
- water, which can, where appropriate, contain pollutants, such as monovalent or polyvalent ions, for example cobalt, iron, chromium, boron or caesium salts, at relatively high concentrations which can range up to 50% or more by weight, even under extreme pH conditions (pH 1);
- solid-phase wastes, in the form of more or less bulky blocks or of pulverised preparations (of particle size which can, for example, be between a few millimeters and a few tens of millimeters), or liquid-phase wastes such as mercurial concrete, mercurial sludges or graphite rods, it being possible for the said wastes to be included with replacement of a portion of the monomer content by water.

The present invention relates, in addition, to:
- an inclusion block of ion exchange resins, obtained by the process as defined above, characterised in that it has been manufactured employing the following amounts of the different products:
  - ion exchange resins: approximately 30 to 75, and preferably 50 to 65, parts by weight, these resins containing an amount of water generally between 40 and 65% by weight;
  - base monomer(s): approximately 25 to 60, and preferably 35 to 50, parts by weight;
  - crosslinking monomer(s): approximately 0.5 to 10, and preferably 1 to 5, parts by weight;
  - possible additional monomer(s): up to 10, and preferably 4 to 8, parts by weight approximately;
- a water-inclusion block containing, where appropriate, at least one pollutant, obtained by the process as defined above, characterised in that it contains, in particular, up to approximately 40% by weight, for example 10–40% by weight, of water included in the form of globules or nodules generally less than 150 μm in diameter;
- an inclusion block of wastes of the mercurial concrete, mercurial sludge or graphite rod type, obtained by the process as defined above, where appropriate with replacement of a portion of the monomer or monomers by water, it then being possible for the said block to have, inter alia, the following composition:
  - wastes : 68 to 70 parts by weight approximately;
  - monomers: 23 to 22 parts by weight approximately;
  - water : 9 to 8 parts by weight approximately.

The present invention also relates to the use of the inclusion blocks as defined above for the storage of industrial pollutants, in particular substances contaminated with radioactive elements, as well as to the use of the water-inclusion blocks, as defined above, as prosthesis materials.

The examples which follow illustrate the present invention: all the amounts are expressed by weight. Dicyclopentadienyloxyethyl methacrylate is designated by the abbreviation DCPOEMA.

EXAMPLES 1 to 12

Inclusion of Ion Exchange Resins

Example 1

25 parts of anion exchange resin possessing a dry extract content of between 35 and 40% and contaminated with radioactive elements, are introduced into a metal cylinder which is at room temperature (20° C.).

With stirring, the following are added:
24.5 parts of DCPOEMA
1 part of 50% benzoyl peroxide
0.5 part of trimethylolpropaneoxyethyl triacrylate
0.025 part of dimethyl-para-toluidine.

The temperature rises to 57° C. in the course of 15 minutes.

An isothermal curing of the mixture is then performed at 57° C. for 3 hours.

The perfectly homogeneous inclusion block possesses a VICAT softening point under 1 kg of 45° C., and a breaking stress of 55 daN/cm$^2$. The VICAT softening is determined according to AFNOR Standard T51021 and the breaking stress according to AFNOR Standard T51101.

Example 2

Example 1 is repeated using the following products:

| | |
|---|---|
| anion exchange resin | 25 parts |
| DCPOEMA | 19.5 parts |
| benzoyl peroxide (50%) | 2 parts |
| trimethylolpropane trimethacrylate | 2 parts |
| cobalt octoate, 6% | 0.5 part |
| dimethyl-para-toluidine | 1 part |

The temperature rises to 70° C. in the course of 1 minute.

After heat curing carried out at 68°–70° C. approximately for 3 hours, the block possesses the following characteristics:
VICAT softening point under 1 kg: 45° C.
breaking stress: 60 daN/cm$^2$

Example 3

Example 1 is repeated employing the following products:

| | |
|---|---|
| anion exchange resin | 25 parts |
| DCPOEMA | 17.5 parts |
| tripropylene glycol diacrylate | 2 parts |
| isobornyl methacrylate | 2 parts |
| cobalt octoate, 6% | 0.5 part |
| benzoyl peroxide, 50% | 2 parts |
| dimethyl-para-toluidine | 1 part |

The temperature rises to 77° C. in the course of 1 minute.

After heat treatment carried out as in the previous examples, the block possesses the following characteristics:

VICAT softening point under 1 kg: 40° C.
breaking stress: 150 daN/cm$^2$

Example 4

The procedure is as in Example 1, using the following products:

| | |
|---|---|
| anion exchange resin | 25 parts |
| DCPOEMA | 17.5 parts |
| methacrylic acid | 2 parts |
| isobornyl methacrylate | 2 parts |
| cobalt octoate, 6% | 0.5 part |
| benzoyl peroxide, 50% | 2 parts |
| dimethyl-para-toluidine | 1 part |

The temperature rises to 71° C. in the course of 1 minute.

VICAT softening point under 1 kg: 30° C.
breaking stress: 30 daN/cm$^2$

Example 5

Example 1 is repeated employing a cation exchange resin:

| | |
|---|---|
| cation exchange resin having 51% dry extract content | 25 parts |
| DCPOEMA | 19.5 parts |
| trimethylolpropane trimethacrylate | 2 parts |
| cobalt octoate, 6% | 0.5 part |
| benzoyl peroxide, 50% | 2 parts |
| dimethyl-para-toluidine | 1 part |

The temperature of the mixture rises to 72° C. in the course of 1 minute.

After heat curing, the block possesses the following characteristics:

VICAT softening point under 1 kg: 48° C.
breaking stress: 66 daN/cm$^2$

Example 6

Example 1 was repeated using the cation exchange resin of Example 5.

| | |
|---|---|
| cation exchange resin | 25 parts |
| DCPOEMA | 17 parts |
| tripropylene glycol diacrylate | 2 parts |
| cobalt octoate, 6% | 0.5 part |
| benzoyl peroxide, 50% | 2 parts |
| dimethyl-para-toluidine | 1 part |

The temperature of the mixture rises to 60° C. in the course of 1 minute.

After heat treatment, the block obtained possesses the following characteristics:

VICAT softening point under 1 kg: 43° C. p1 breaking stress: 265 daN/cm$^2$

Example 7

Example 6 is repeated employing the following ingredients:

| | |
|---|---|
| cation exchange resin | 25 parts |
| DCPOEMA | 19.5 parts |
| trimethylolpropane triacrylate | 2 parts |
| cobalt octoate, 6% | 0.5 part |
| benzoyl peroxide, 50% | 2 parts |
| dimethyl-para-toluidine | 1 part |

The temperature of the mixture rises to 76° C. in the course of 1 minute.

After heat treatment as in Example 1, the block obtained possesses the following characteristics:

VICAT softening point under 1 kg: 60° C.
compressive breakage strength: 180 daN/cm$^2$

Example 8

Example 1 is repeated:

| | |
|---|---|
| cation exchange resin | 25 parts |
| DCPOEMA | 17.5 parts |
| tripropylene glycol diacrylate | 2 parts |
| isobornyl methacrylate | 2 parts |
| cobalt octoate, 6% | 0.5 part |
| benzoyl peroxide, 50% | 2 parts |
| dimethyl-para-toluidine | 1 part |

The temperature of the mixture rises to 68° C. in the course of 1 minute.

VICAT softening point under 1 kg: 50° C.
compressive breakage strength: 70 daN/cm$^2$

Example 9

Example 1 is repeated employing a mixture of contaminated ion exchange resins:

| | |
|---|---|
| anion exchange resin | 15 parts |
| cation exchange resin | 10 parts |
| DCPOEMA | 17.5 parts |
| tripropylene glycol diacrylate | 2 parts |
| isobornyl methacrylate | 2 parts |
| cobalt octoate, 6% | 0.5 part |
| benzoyl peroxide, 50% | 2 parts |
| dimethyl-para-toluidine | 1 part |

The temperature of the mixture rises to 76° C. in the course of 1 minute.

After heat treatment carried out as in Example 1, the block obtained possesses the following characteristics:

VICAT softening point under 1 kg: 40° C.
compressive breakage strength: 60 daN/cm$^2$

Example 10

Example 1 is repeated employing the Following ingredients:

| | |
|---|---|
| cation exchange resin | 25 parts |
| DCPOEMA | 17 parts |
| isobornyl acrylate | 3 parts |
| tripropylene glycol diacrylate | 1 part |
| trimethylolpropane triacrylate | 1 part |
| benzoyl peroxide, 50% | 1 part |
| dimethyl-para-toluidine | 0.5 part |

The temperature of the mixture rises to 72° C. in the course of 1 minute.

VICAT softening point under 1 kg: 52° C.
compressive breakage strength: 190 daN/cm$^2$

Example 11

Example 1 is repeated using the following products:

| | |
|---|---|
| cation exchange resin | 25 parts |
| DCPOEMA | 17 parts |
| isobornyl acrylate | 3 parts |
| tripropylene glycol diacrylate | 1 part |
| trimethylolpropane triacrylate | 1 part |
| benzoyl peroxide, 50% | 2 parts |
| dimethyl-para-toluidine | 0.25 part |

The temperature of the mixture rises to 75° C. in the course of 2 minutes.
VICAT softening point under 1 kg: 55° C.
compressive breakage strength: 175 daN/cm$^2$ Example 12

Example 1 is repeated employing:

| | |
|---|---|
| cation exchange resin | 25 parts |
| epoxidised DCPOEMA | 17 parts |
| isobornyl acrylate | 3 parts |
| tripropylene glycol diacrylate | 1 part |
| trimethylolpropane triacrylate | 1 part |
| benzoyl peroxide, 50% | 2 parts |
| dimethyl-para-toluidine | 1 part |

The temperature of the mixture rises to 80° C. in the course of 3 minutes.
VICAT softening point under 1 kg: 45° C.
compressive breakage strength: 145 daN/cm$^2$ EXAMPLES 13 to 16

Production of Water-Inclusion Blocks

For each example, two inclusion blocks were prepared, containing 30% and 40% by weight of water, respectively.

General Procedure

The monomer mixture containing DCPOEMA, the possible crosslinking agents (tripropylene glycol diacrylate, trimethylolpropane triacrylate or trimethylolpropane trimethacrylate), the possible monomer (isobornyl acrylate) and benzoyl peroxide were introduced into a polyethylene or iron vessel. The mixture was stirred for 15 minutes so as to create a sufficiently stable emulsion for polymerisation, while the temperature was brought to 20° C.±1° C. Dimethyl-para-toluidine was then added, the mixture was stirred for 2 minutes and stirring was then stopped. The progress of the polymerisation was monitored by measuring the temperature of the reaction medium with time: after a period of inhibition of polymerisation of a few minutes, during which the temperature remains constant, the temperature increases rapidly to reach a maximum value below 100° C. It then decreases slowly to room temperature.

A pinkish beige, homogeneous block displaying no trace of exudation of water is thereby obtained. To avoid the presence of any residual monomers, a postcuring of 15 hours at 70° C. was performed in every case.

The different compositions of the reaction mixtures employed are as follows:

TABLE 1

| Composition of the reaction mixture* | 13 | 14 | 15 | 16 |
|---|---|---|---|---|
| DECPOEMA | 340 | 340 | 440 | 340 |
| Isobornyl acrylate | 60 | 60 | | 60 |
| Tripropylene glycol diacrylate | 20 | | | |
| Trimethylol propane triacrylate | | 20 | | |
| Trimethylolpropane trimethacrylate | | | 40 | |
| Benzoyl peroxide | 5 | 5 | 5 | 5 |
| Dimethyl-para-toluidine | 1 | 1 | 1 | 1 |

*in parts by weight

Examination of the morphology of the materials by scanning electron microscopy shows that these materials are filled with holes whose size is 150 μm at most, the population of holes increasing with the percentage of water. Hence the water is indeed embedded in the polymer matrix, being present in the latter in the form of small globules.

Moreover, the hardness of the material (VICAT point) increases with the percentage of water, as does the maximum stress on crushing:

| | maximum stress |
|---|---|
| 30% of water | 18.1 MPa |
| 40% of water | 23.4 MPa, | which suggests that the globules of water behave like a filler imparting impact and compressive strength to the material.

The good compatibility of DCPOEMA with water, its safety with respect to human beings and its absence of water loss makes these composites useful in the field of prostheses.

EXAMPLES 17 to 20

Inclusion of Various Wastes

Example 17

Inclusion of Various Mercurial Sludges Which Can Contain up to 75% of Water

The following composition is prepared:

| | |
|---|---|
| DCPOEMA | 340 parts |
| isobornyl acrylate | 60 parts |
| trimethylolpropane trimethacrylate | 40 parts |

500 g of sludges were introduced with stirring into 500 g of this monomer mixture. The mixture was left to emulsify with stirring for between 10 and 30 minutes.

0.5 to 1% of benzoyl peroxide relative to the monomer mixture was then introduced, the mixture was stirred for 5 to 15 minutes and 0.1 to 0.4% of dimethyl-para-toluidine relative to the monomer mixture was then added.

Stirring was stopped, depending on the catalytic systems, after 2 to 6 minutes.

Example 18

Inclusion of Various Pulverised Mercurial Concretes Having a Variable Moisture Content The procedure was the same as in Example 17, replacing the sludges by various pulverised concretes charged to the extent of 50 to 60%.

Example 19

Inclusion of Various Blocks of Mercurial Concretes

The concrete blocks were introduced into a first vessel. DCPOEMA or a mixture of DCPOEMA and comonomers such as isobornyl acrylate, with or without crosslinking monomers, was introduced into a second vessel, the mixture was stirred, 0.5 to 1% of benzoyl peroxide relative to the monomer mixture was then added, the mixture was stirred for a further 10 minutes and 0.1 to 0.4% of dimethyl-para-toluidine relative to the monomer mixture was then added. The concrete/monomer mixture ratio is between 60:40 and 70:30.

The reaction mixture is then poured into the first vessel to cover the concrete blocks. Depending on the temperature of the medium, setting takes place in between 5 and 60 minutes.

Example 20

Inclusion of Blocks or Pulverised Preparations of Graphite Rods Having a Variable Moisture Content The procedures of Examples 18 and 19 are reproduced to obtain blocks comprising the inclusion of 50 to 70% of graphite rods.

Referring to the epoxidized DCPOEMA of Example 12, the compound is of the formula:

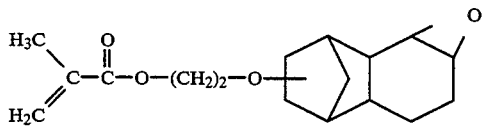

The above epoxide can be produced, for example, according to published French Application No. 90/08607, filed Jul. 6, 1990, corresponding to commonly assigned, allowed U.S. patent application Ser. No. 07/725,318, filed Jul. 8, 1991.

With respect to the term "block" or "blocks" employed in the description of the invention, these terms are meant to be synonymous with "particle" or "particles", but are not limited to pieces and lumps of irregular, and random shapes, as well as geometric shapes, such as, for example, spheres, cylinders, particles having at least one flat surface, and the like.

As for the use of the inclusion blocks for the storage of radioactive materials, the blocks can be stored conventionally under varying non-critical conditions of temperature and humidity. As for the use of water-inclusion blocks for prostheses, the blocks would be molded, cast, milled, or ground to the desired shape according to conventional methods.

The entire disclosure of all applications, patents, and publications, cited herein, and of corresponding French Application 92/01638, filed Feb. 13, 1992, are hereby incorporated by reference.

The preceding examples can be repeated with similar success by substituting the generically or specifically described reactants and/or operating conditions of this invention for those used in the preceding examples.

From the foregoing description, one skilled in the art can easily ascertain the essential characteristics of this invention and, without departing from the spirit and scope thereof, can make various changes and modifications of the invention to adapt it to various usages and conditions.

We claim:

1. A process for inclusion in a resin of at least one substance of liquid to solid consistency, comprising embedding said at least one substance in a (meth)acrylic resin obtained in situ by direct polymerization, without prior preparation of a prepolymer syrup, using a monomer system based on at least one (meth)acrylic monomer possessing a boiling point between 330° C. and 380° C., wherein said at least one substance and the monomers of the resultant resin are mixed, then at least one polymerization initiator, at least one activator, and optionally at least one transfer agent are added, the resultant mixture is stirred and the temperature of the stirred mixture increases to at most 100° C. after not more than 40 minutes, and polymerization is allowed to proceed to completion, whereby a (meth)acrylic resin inclusion particle in which said at least one substance is embedded is obtained, and wherein the inclusion particle resulting from said in situ polymerization is subjected to a postcuring at a temperature of between 50° C. and 85° C. for a period of 2 to 15 hours.

2. A process according to claim 1, wherein said monomer system contains at least one (meth)acrylic monomer having a boiling point of between 330° C. and 380° C., selected from dicyclopentadienyloxyethyl methacrylate and its epoxidized homologue, and optionally at least one crosslinking monomer selected from di- and tri(meth)-acrylates.

3. A process according to claim 1, wherein said monomer system additionally contains at least one comonomer selected from isobornyl methacrylate, isobornyl acrylate, acrylic acid and methacrylic acid.

4. A process according to claim 2, further comprising adding to said monomer system at least one thickening agent selected from (meth)acrylic oligomers.

5. A process according to claim 2, wherein said at least one polymerization initiator is selected from peroxides and percarbonates, and said at least one activator is selected from tertiary amines and organometallic activators.

6. A process according to claim 2, wherein said substance comprises at least one of:

an ion exchange resin contaminated with a radioactive element;

water, optionally containing pollutants comprising cobalt, iron, chromium, boron or cesium salts; and solid-phase wastes, in the form of particles or pulverized preparations, or liquid-phase wastes comprising mercurial concrete, mercurial sludges or graphite rods.

7. An inclusion particle of ion exchange resin contaminated with a radioactive element, obtained by a process comprising embedding said resin contaminated with a radioactive element in a (meth)acrylic resin obtained in situ by direct polymerization, without prior preparation of a prepolymer syrup, using a monomer system based on at least one (meth)acrylic monomer possessing a boiling point between 330° C. and 380° C., wherein said resin contaminated with a radioactive element and the monomers of the resultant (meth)acrylic resin are mixed, then at least one polymerization initiator, at least one activator, and optionally at least one transfer agent are added, the resultant mixture is stirred and the temperature of the stirred mixture increases to at most 100° C. after not more than 40 minutes, and polymerization is allowed to proceed to completion, whereby a (meth)acrylic resin inclusion particle in which said resin contaminated with a radioactive element is embedded is obtained;

wherein said monomer system contains at least one (meth)acrylic monomer having a boiling point of between 330° C. and 380° C., selected from dicyclopentadienyloxyethyl methacrylate and its epoxidized homologue, and optionally at least one cross-linking monomer selected from di- and tri(meth)acrylates; and wherein said inclusion particle of said ion exchange resin contaminated with a radioactive element is produced from the following amounts:

ion exchange resin: 30 to 75 parts by weight, said resins containing an amount of water between 40% and 65% by weight;

base monomer(s); 25 to 60 parts by weight;

crosslinking monomer(s): 0.5 to 10 parts by weight; and optional comonomers: 0 to 10 parts by weight.

8. A water-inclusion particle, optionally containing at last one pollutant, obtained by a process comprising embedding water optionally containing at least one pollutant in a (meth)acrylic resin obtained in situ by direct polymerization, without prior preparation of a prepolymer syrup, using a monomer system based on at least one (meth)acrylic monomer possessing a boiling point between 330° C. and 380° C., wherein said water optionally containing at least one pollutant and the monomers of the resultant (meth)acrylic resin are mixed, then at least one polymerization initiator, at least one activator, and optionally at least one transfer agent are added, the resultant mixture is stirred and the temperature of the stirred mixture increases to at most 100° C. after not more than 40 minutes, and polymerization is allowed to proceed to completion, whereby a (meth)acrylic resin inclusion particle in which said water optionally containing at least one pollutant is embedded is obtained;

wherein said monomer system contains at least one (meth)acrylic monomer having a boiling point of between 330° C. and 380° C., selected from dicyclopentadienyloxyethyl methacrylate and its epoxidized homologue, and optionally at least one cross-linking monomer selected from di- and tri(meth)acrylates; and wherein said at least one pollutant is selected from cobalt, iron, chromium, boron and cesium salts; and said water-inclusion particle contains not more than 40% by weight of water included in the form of globules or nodules less than 150 μm in diameter.

9. A inclusion particle containing waste particles, pulverized waste preparations or liquid waste selected from mercurial concrete, mercurial sludge or graphite rod, obtained by a process comprising embedding said waste in a (meth)acrylic resin obtained in situ by direct polymerization, without prior preparation of a prepolymer syrup, using a monomer system based on at least one (meth)acrylic monomer possessing a boiling point between 330° C. and 380° C., wherein said waste and the monomers of the resultant (meth)acrylic resin are mixed, then at least one polymerization initiator, at least one activator, and optionally at least one transfer agent are added, the resultant mixture is stirred and the temperature of the stirred mixture increases to at most 100° c. after not more than 40 minutes, and polymerization is allowed to proceed to completion, whereby a (meth)acrylic resin inclusion particle in which said waste is embedded is obtained;

wherein said monomer system contains at least one (meth)acrylic monomer having a boiling point of between 330° C. and 380° C., selected from dicyclopentadienyloxyethyl methacrylate and its epoxidized homologue, and optionally at least one cross-linking monomer selected from di- and tri(meth)acrylates; and wherein said inclusion particle contains:

wastes: 68 to 70 parts by weight;

monomers: 23 to 22 parts by weight; and water: 9 to 8 parts by weight.

10. A process according to claim 2, wherein said crosslinking monomer is present and is selected from the group consisting of trimethylolpropane trimethacrylate, hexanediol diacrylate, trimethylolpropaneoxyethyl triacrylate, glyceroltrioxypropyl triacrylate, ethylene glycol dimethacrylate, and tripropylene glycol diacrylate.

11. An inclusion particle according to claim 7, wherein the amount of ion exchange resin is 50–65 parts by weight, the amount of base monomer is 35–50 parts by weight, and the amount of crosslinking monomer is 1–5 parts by weight.

12. An inclusion particle according to claim 11, produced with 4–8 parts by weight of a comonomer selected from the group consisting of isobornyl methacrylate, isobornyl acrylate, acrylic acid, and methacrylic acid.

13. A method of entrapping contaminated waste containing a radioactive ion exchange resin, comprising embedding said ion exchange resin in a polymer of dicyclopentadienyloxyethyl methacrylate or an epoxidized homolog thereof.

14. A method according to claim 13, wherein the ion exchange resin is a cationic resin.

15. A process according to claim 4, wherein said thickening agent is bisphenol diglycidyl dimethacrylate or bisphenol diglycidyl fumarate.

16. A process according to claim 5, wherein said initiator is benzoyl peroxide, said activator is dimethyl-para-toluidine, and said monomer having a boiling point between 330° C. and 380° C. is dicyclopentadienyloxyethyl methacrylate.

17. A process according to claim 2, wherein said substance comprises at least one of:

an ion exchange resin contaminated with a radioactive element;

water; and solid-phase wastes, in the form of particles or pulverized preparations, or liquid-phase wastes comprising mercurial concrete, mercurial sludges or graphite rods.

18. A water-inclusion particle obtained by the process of claim 8, wherein said water does not contain pollutants and said particle contains not more than 40% by weight of water included in the form of globules or nodules less than 150 μm in diameter.

19. A method of employing a water-inclusion particle has a prosthesis material, comprising:

molding at least one water-inclusion particle according to claim 18 into a prosthesis form.

* * * * *